April 4, 1950 A. L. MARTIN Plant Pat. 930

PEACH TREE

Filed Jan. 17, 1949

WITNESS

Addison E. Avery

INVENTOR

Allen L. Martin

Webster & Webster

ATTYS.

Patented Apr. 4, 1950

Plant Pat. 930

UNITED STATES PATENT OFFICE

930

PEACH TREE

Allen L. Martin, Winters, Calif.

Application January 17, 1949, Serial No. 71,299

1 Claim. (Cl. 47—62)

The present discovery relates to a new and distinct variety of peach tree which bears freestone fruit.

Such fruit is a yellow peach, having a red cheek, and solid texture, with excellent keeping and shipping qualities. By reason of its solid texture the peach can be lye peeled, when fully ripe, for canning, and in addition the peach is excellent for freezing and drying.

The fruit is similar to a Rio Oso Gem freestone, although it ripens approximately one week earlier, and with the last of the Elbertas.

The suture of the present peach is rounder and smoother than the Rio Oso Gem, and is more like the J. H. Hale in shape. Like the J. H. Hale, the instant variety bears a sterile blossom, but when properly pollenized a heavy crop of large size fruit is produced.

The variety originated as a seedling on the ranch of applicant near Winters, California, and since its discovery such variety has been asexually reproduced; the reproduced trees carrying forward all the new and distinctive characteristics of the original or parent tree.

Careful observation of the reproductions, which are growing in the University of California Orchard, at Winters, California, and comparison of such reproductions with the parent tree and its fruit, gives full support to the fact that the novel characteristics exist and remain true in said reproductions.

Figures 1, 2:
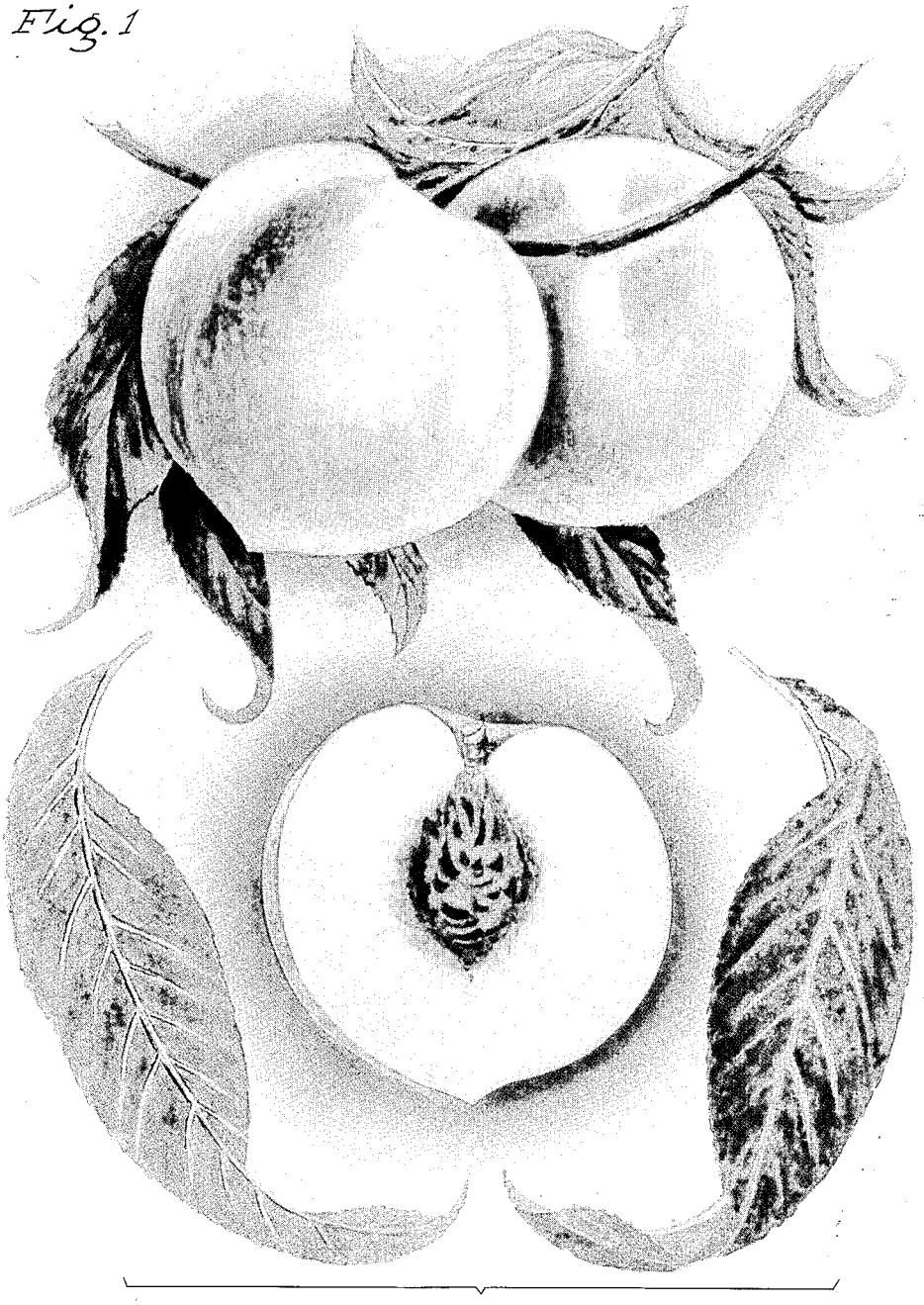
Fig. 1 is a perspective view of a pair of the peaches attached to a twig bearing leaves.
Fig. 2 is a sectional view, taken axially with the stone exposed, of a peach of the variety in association with detached leaves.

Referring now in detail to the new and distinct variety of peach tree, the following is a specific description, in outline, of such tree and its fruit:

Tree: Medium size; medium vigorous; upright, spreading: dense-open. Vase formed. Productive; regular bearer.

Trunk: Medium size; medium surface.

Branches: Medium size; medium surface. Brown, dull.

*Lenticels.* — Numerous-medium. Medium size.

Leaves: Average length, 6″–7½″; average width, 1½″–1⅓″; medium size. Acuminate, lanceolate; acutely pointed; medium thickness. Dark green; smooth.

*Margin.*—Glandular, crenate.

*Petiole.*—Medium length; thick.

*Glands.*—Average number, 2–5. Opposite-alternate; large-medium. Reniform. Position—base blade and on petiole.

Flower buds: Medium size; long; conic, pointed, plump. Free. Pubescent.

Flowers: Medium blooming date as compared with other varieties. Large. Pink.

Fruit: Maturity when described, eating ripe.

*Size.*—Uniform; large, medium. Average axial diameter, 2¾″ to 3″; average transverse in suture plane, 3 to 3¼″.

*Form.*—Uniform; globose; compressed towards suture.

*Suture.*—An inconspicuous line with slight depression beyond pistil point.

*Ventral surface.*—Rounded slightly; lipped throughout; lips equal.

*Cavity.*—Flaring, rounded; elongated in suture plane with suture showing on one side.

*Base.*—Rounded; truncate; very slightly oblique.

*Apex.*—Rounded; pistil point—apical.

Skin: Thin. No tendency to crack.

*Down.*—Moderate, medium length.

*Color.*—Deep rich clear yellow ground color; blushed deep red where exposed and obscurely streaked or striped darker red or purplish red; semi-blushed red on most of protected surface; often without blush where a leaf or twig has protected the surface.

Flesh: Yellow, streaked with red next to stone. Surface of pit cavity—red with yellow fibers.

*Amygdalin.*—Scant.

*Juice.*—Abundant—moderate. Rich.

*Texture.*—Firm or solid; fine.

*Fibres.*—Few.

*Ripens.*—Evenly.

*Flavor.*—Sub-acid, mild.

*Aroma.*—Pronounced.

*Eating quality.*—Good.

Stone: Free.

*Fibres.*—Short.

*Parts from flesh.*—Smoothly.

*Size.*—Medium—small. Average length, 1¼″ to 1⅜″; average breadth, 1″ to 1⅜″; average thickness, ¾″.

*Form.*—Globose-oval.

*Base.*—Straight-oblique.

*Hilum.*—Oval.

*Apex.*—Rounded, truncate.

*Sides.*—Equal.

*Surface.*—Regularly furrowed toward apex; pitted toward base.

*Ridges.*—Rounded; jagged toward apex.

*Pits.*—Elongated.

*Dorsal edge.*—Narrow with deep narrow groove toward base to above center.

*Color of stone.*—Dark brown, flushed red, especially basally along sutures.

*Tendency to split.*—Slight.

The fruit is an excellent market and dessert peach, and its firm or solid texture, though fine, permits of its lye peeling, when ripe, for canning. Additionally, the peach is excellent for freezing or drying.

The peach ripens at a desirable time, being approximately one week ahead of the Rio Oso Gem and substantially with the last of the Elbertas.

In the 1948 season the dates of first and last picking were approximately August 10th and 20th, respectively.

The tree and its fruit as herein described may vary in slight details due to climatic and soil conditions under which the variety may be grown.

Having thus described my invention I claim:

A new and distinct variety of peach tree, substantially as shown and described, having sterile blossoms like the J. H. Hale, but when properly pollenized bearing a heavy crop of large size, yellow fleshed freestone fruit; said fruit being characterized by its similarity to, but ripening approximately one week earlier than, the Rio Oso Gem, and with the last of the Elbertas; its suture which is rounder and smoother than the Rio Oso Gem, and more like the J. H. Hale in shape; its firm but fine texture; its excellency for market, dessert, canning, freezing, and drying use; its excellent shipping and keeping qualities; and the attractive color of the skin, which is deep rich clear yellow ground color, blushed deep red where exposed, and obscurely streaked or striped darker red, and semi-blushed red on most of its protected surface.

ALLEN L. MARTIN.

No references cited.